United States Patent [19]

Senn-Bilfinger et al.

[11] Patent Number: 5,665,730

[45] Date of Patent: Sep. 9, 1997

[54] PHARMACEUTICALLY USEFUL IMIDAZOPYRIDINES

[75] Inventors: Jörg Senn-Bilfinger; Gerhard Grundler; Georg Rainer, all of Konstanz, Germany

[73] Assignee: BYK Gulden Lomberg Chemische Fabrik GmbH, Konstanz, Germany

[21] Appl. No.: 505,271

[22] PCT Filed: Feb. 7, 1994

[86] PCT No.: PCT/EP94/00335

§ 371 Date: Aug. 15, 1995

§ 102(e) Date: Aug. 15, 1995

[87] PCT Pub. No.: WO94/18199

PCT Pub. Date: Aug. 18, 1994

[30] Foreign Application Priority Data

Feb. 15, 1993 [CH] Switzerland ................ 453/93
Jun. 29, 1993 [CH] Switzerland ................ 1945/93

[51] Int. Cl.$^6$ ................ A16K 31/435; C07D 471/04
[52] U.S. Cl. ................ 514/300; 546/121
[58] Field of Search ................ 546/121; 514/300

[56] References Cited

FOREIGN PATENT DOCUMENTS

| 33094 | 8/1981 | European Pat. Off. . |
|---|---|---|
| 204785 | 12/1986 | European Pat. Off. . |
| 228006 | 8/1987 | European Pat. Off. . |
| 268989 | 6/1988 | European Pat. Off. . |
| 308917 | 3/1989 | European Pat. Off. . |

*Primary Examiner*—Bernard Dentz
*Attorney, Agent, or Firm*—Jacobson, Price, Holman & Stern, PLLC

[57] ABSTRACT

The invention relates to novel compounds of the formula I

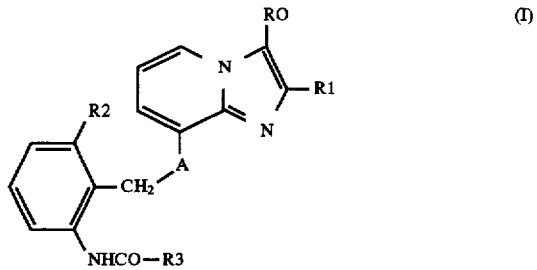

and the therapeutic use thereof.

9 Claims, No Drawings

PHARMACEUTICALLY USEFUL IMIDAZOPYRIDINES

This application is a 371 of PCT/EP94/00335 filed Feb. 7, 1994.

FIELD OF THE INVENTION

The invention relates to novel imidazopyridines which are intended for use in the pharmaceutical industry as active substances for producing pharmaceuticals.

BACKGROUND OF THE INVENTION

European Patent Application EP-A-0 033 094 describes imidazo[1,2-a]pyridines which have in position 8 an aryl substituent which is preferably a phenyl, thienyl or pyridyl radical or a phenyl radical which is substituted by chlorine, fluorine, methyl, tert.-butyl, trifluoromethyl, methoxy or cyano. Aryl radicals mentioned as particularly interesting in EP-A-0 033 094 are the radicals phenyl, o- or p-fluorophenyl, p-chlorophenyl and 2,4,6-trimethylphenyl, of which the radicals phenyl, o- or p-fluorophenyl and 2,4,6-trimethylphenyl are particularly preferred. European Patent Applications EP-A-0 204 285, EP-A-0 228 006, EP-A-0 268 989 and EP-A-0 308 917 describe imidazo[1,2-a]pyridines which have in position 3 an unsaturated aliphatic radical, in particular a (substituted) alkynyl radical. European Patent Application EP-A-0 266 890 describes imidazo[1,2-a]pyridines which are substituted in position 8 by an alkenyl, alkyl or cycloalkylalkyl radical.

DESCRIPTION OF THE INVENTION

It has now been found that the compounds which are described in detail hereinafter and which differ from the compounds of the prior art, in particular by the substitution in position 3 or 8, have surprising and particularly advantageous properties.

The invention relates to compounds of the formula I (see the end of this specification)
in which R0 denotes methyl or hydroxymethyl, R1 denotes 1–4C-alkyl, R2 denotes 1–4C-alkyl, R3 denotes 1–4C-alkoxy and A denotes O (oxygen) or NH,
and the salts thereof.

1–4C-alkyl represents straight-chain or branched alkyl radicals with 1 to 4 carbon atoms. Examples which may be mentioned are the butyl, iso-butyl, sec.-butyl, tert.-butyl, propyl, isopropyl, ethyl and, in particular, the methyl radical.

1–4C-alkoxy represents an oxygen atom to which one of the abovementioned 1–4C-alkyl radicals is bonded. The methoxy radical is preferred.

Suitable salts for compounds of the formula I are preferably all acid addition salts. Particular mention may be made of the pharmacologically compatible salts of the inorganic and organic acids customarily used in pharmaceutical technology. Pharmacologically incompatible salts which may, for example, be the initial products of the processes for the preparation of the compounds according to the invention on an industrial scale are converted into pharmacologically compatible salts by processes known to the skilled worker. Suitable as such are water-soluble and water-insoluble acid addition salts with acids, such as hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed for the preparation of the salts in a ratio of amounts which is equimolar or different therefrom—depending on whether the acid is mono- or polybasic and depending on which salt is required.

Examples of preferred compounds which may be mentioned are the compounds 3-hydroxymethyl-8-(2-methoxycarbonylamino-6-methylbenzylamino)-2-methylimidazo[1,2-a]pyridine, 3-hydroxymethyl-8-(2-methoxycarbonylamino-6-methylbenzyloxy)-2-methylimidazo[1,2-a]pyridine, 8-(2-methoxycarbonylamino-6-methylbenzylamino)-2,3-dimethylimidazo[1,2-a]pyridine and 8-(2-methoxycarbonylamino-6-methylbenzyloxy)-2,3-dimethylimidazo[1,2-a]pyridine and the salts thereof.

The invention further relates to a process for the preparation of the compounds of the formula I and the salts thereof. The process comprises a) for the preparation of the compounds of the formula I, in which R0 denotes hydroxymethyl, reducing compounds of the formula II (see attached sheet of formulae), in which R1, R2, R3 and A have the abovementioned meanings, or comprises b) for the preparation of the compounds of the formula I, in which R0 denotes methyl, reacting compounds of the formula III (see attached sheet of formulae), in which R1 and A have the abovementioned meanings, with compounds of the formula IV (see attached sheet of formulae), in which R2 and R3 have the abovementioned meanings and X denotes a suitable leaving group, or comprises c) for the preparation of the compounds of the formula I, in which R0 denotes methyl, reacting compounds of the formula V (see attached sheet of formulae), in which R1, R2 and A have the abovementioned meanings, with compounds of the formula VI (see attached sheet of formulae), wherein R3 has the abovementioned meanings and Y denotes a suitable leaving group, and, if required, subsequently converting the resulting compounds I into the salts thereof, or comprises, if required, subsequently liberating the compounds I from the resulting salts of the compounds I.

The reduction of the compounds II is carried out in a manner familiar to the skilled worker. It takes place in inert solvents, for example lower aliphatic alcohols, for example by use of suitable hydrides, such as sodium borohydride, if desired with the addition of water.

The reaction of the compounds III with the compounds IV is carried out in a manner familiar to the skilled worker, for example by analogous Application of processes such as those described in European Patent Applications EP-A-0 033 094 or EP-A-0 308 917. A suitable leaving group is, for example, a halogen atom (preferably chlorine or bromine) or a methanesulfonyloxy group. The reaction is carried out advantageously in the presence of a base (e.g. of an inorganic hydroxide, such as sodium hydroxide, or of an inorganic carbonate, such as potassium carbonate, or of an organic nitrogen base, such as triethylamine, pyridine, collidin or 4-dimethylaminopyridine), in which the course of the reaction can be assisted by the addition of catalysts, such as alkali iodide or tetrabutylammonium bromide.

The reaction of the compounds V with the compounds VI is also carried out in a manner familiar to the skilled worker as it is customary for the preparation of aromatic urethans, preferably by reacting the compounds V with haloformiates (Y=halogen), such as chloroformiates, in inert solvents. The reaction is advantageously carried out in the presence of an acid binding agent (proton acceptor). As proton acceptors, alkali metal carbonates (such as potassium carbonate) or hydrogen carbonates (such as sodium hydrogen carbonate), or tertiary amines (such as triethylamine) may be mentioned for example.

The skilled worker is aware because of his expert knowledge of the specific reaction conditions required for carrying out the process.

The substances according to the invention are isolated and purified in a manner known per se, for example in such a way that the solvent is removed by distillation in vacuo, and the resulting residue is recrystallized from a suitable solvent or subjected to one of the conventional purification methods such as, for example, column chromatography on suitable support material.

Acid addition salts are obtained by dissolving the free base in a suitable solvent, for example in a chlorinated hydrocarbon, such as methylene chloride or chloroform, or a lower aliphatic alcohol (ethanol, isopropanol), a ketone, such as acetone, or an ether, such as tetrahydrofuran or diisopropylether, which contains the required acid or to which the required acid is subsequently added.

The salts are isolated by filtration, reprecipitation, precipitation with a non-solvent for the addition salt or by evaporating off the solvent. Resulting salts can be converted by rendering alkaline, for example with aqueous ammonia solution, into the free bases which can, in turn, be converted into acid addition salts. It is possible in this way to convert pharmacologically incompatible acid addition salts into pharmacologically compatible acid addition salts.

The starting compounds II can be prepared in a manner known per se, for example by reacting the compounds VII with the compounds VIII (see attached sheet of formulae) in which R1, R2, R3 and A have the abovementioned meanings, and X is a suitable leaving group, for example a halogen atom (preferably chlorine or bromine), or by analogous application of processes, such as those described, for example, in European Patent Applications EP-A-0 033 094 or EP-A-0 308 917.

The starting compounds III are known from European Patent Application EP-A-0 299 470, the starting compounds IV from European Patent Application EP-A-0 308 917.

The starting compounds V can be prepared in a manner known per se from the corresponding nitro compounds by reduction. The nitro compounds themselves can be prepared from the compounds III and appropriate nitro compounds corresponding with the compounds IV.

The following examples serve to explain in detail the preparation of the compounds according to the invention. In particular, the examples serve to exemplary describe the reactions according to the process variants a, b and c as well as the preparation of selected starting compounds. Likewise, further compounds of the formula I as well as further starting compounds, the preparation of which is not described explicitly, can be prepared in an analogous manner or in a manner familiar to the skilled worker by applying usual process techniques. The abbreviation RT stands for room temperature, h stands for hour(s), m.p. for melting point, dec. for decomposition.

EXAMPLES

1. 3-Formyl-8-(2-methoxycarbonylamino-6-methylbenzylamino)-2-methylimidazo[1,2-a]pyridine A suspension of 400 mg of commercial 80% sodium hydride in 10 ml of dry tetrahydrofuran is added to a solution of 2 g of 8-amino-3-formyl-2-methylimidazo[1,2-a]pyridine in 40 ml of dry tetrahydrofuran at RT. Brief heating at 50° C. is followed by vigorous evolution of gas. After the evolution of gas is complete, the mixture is cooled to 0° C., and a solution of 3.9 g of 2-methoxycarbonylamino-6-methylbenzyl bromide in 40 ml of dry tetrahydrofuran is added dropwise. The mixture is again heated to 50° C. and kept at this temperature for 3 h. It is then poured into ice-water, neutralized with a little dilute hydrochloric acid and extracted four times with ethyl acetate. The collected organic phases are washed with water and dried over sodium sulfate. The solvent is stripped off in vacuo, and the dark brown viscous residue is chromatographed on silica gel (ethyl acetate:petroleum ether=1:1 as eluent). Recrystallization from isopropanol results in 2.5 g of the title compound of m.p. 188°–190° C. (dec.).

2. 3-Hydroxymethyl-8-(2-methoxycarbonylamino-6-methylbenzylamino)-2-methylimidazo[1,2-a]pyridine 2 g of 3-formyl-8-(2-methoxycarbonylamino-6-methylbenzylamino)-2-methylimidazo[1,2-a]pyridine are suspended in 30 ml of methanol at RT, 0.2 g of sodium borohydride is added in portions, and the mixture is stirred at RT for 1 h. Subsequently, half the solvent is stripped off in vacuo, the residue is poured into ice-water, and the mixture is neutralized with a few drops of dilute hydrochloric acid and extracted four times with ethyl acetate. The collected organic phases are washed with water and dried over sodium sulfate. The solvent is stripped off in vacuo. The remaining yellowish residue completely crystallizes after some time. Recrystallization from ethyl acetate results in 1.3 g of the title compound of m.p. 170°–172° C.

3. 3-Formyl-8-(2-methoxycarbonylamino-6-methylbenzyloxy)-2-methylimidazo[1,2-a]pyridine 2.6 g of 3-formyl-8-hydroxy-2-methylimidazo[1,2-a]pyridine are dissolved in 50 ml of dry acetonitrile with exclusion of moisture at 50° C. and, after cooling to RT, 2.8 g of commercial potassium fluoride (50% by weight) on kieselguhr (for example Celite®) are added. A solution of 3.6 g of 2-methoxycarbonylamino-6-methylbenzyl bromide in 50 ml of dry acetonitrile is added dropwise, and the mixture is heated at 70° C. for 6 h. After cooling to RT, the mixture is poured into ice-water, adjusted to pH 9 with a few drops of 6N sodium hydroxide solution and extracted with ethyl acetate. The collected organic phases are washed with water and dried over sodium sulfate. Stripping off the solvent in vacuo and stirring in a little cold methanol result in 3.2 g of the title compound of m.p. 196°–198° C.

4. 3-Hydroxymethyl-8-(2-methoxycarbonylamino-6-methylbenzyloxy)-2-methylimidazo[1,2-a]pyridine In analogy to Example 2, 2.1 g of the title compound of m.p. 185°–187° C. are obtained from 3 g of 3-formyl-8-(2-methoxycarbonylamino-6-methylbenzyloxy)-2-methylimidazo[1,2-a]pyridine and 400 mg of sodium borohydride.

5. 8-(2-Methoxycarbonylamino-6-methylbenzylamino)-2,3-dimethylimidazo[1,2-a]pyridine 4.5 g of sodium iodide and 6.63 g of dry sodium carbonate are added to a solution of 4.03 g of 8-amino-2,3-dimethylimidazo[1,2-a]pyridine and 6.41 g of 2-methoxycarbonylamino-6-methyl-benzyl chloride in 400 ml of dry acetone, and the mixture is heated under reflux for 6 h. After cooling to RT, 400 ml of water are added and the acetone is distilled off in a water jet vacuum. The aqueous residue is then extracted three times with each time 200 ml of ethyl acetate. The combined organic extracts are washed with 300 ml of water, dried over magnesium sulfate and then concentrated. The residue is purified by chromatography on silica gel (toluene/dioxan=9:1 as eluent). The fractions with $R_f$=0.2 are concentrated and then recrystallized from diisopropyl ether. 4.71 g (56%) of the title compound of m.p. 136°–138° C. are isolated.

a) By reacting the title compound, dissolved in acetone, with 12N hydrochloric acid, the hydrochloride of the title compound of m.p. 211°–212° C. (dec.) is obtained.

b) By reacting the title compound, dissolved in tetrahydrofuran, with methanesulfonic acid, the methanesulfonate of the title compound of m.p. 181°–182° C. (dec.) is obtained.

c) By reacting the title compound, dissolved in acetone, with fumaric acid, the hemifumarate of the title compound of m.p. 191°–192° C. (dec.) is obtained.

6. 8-(2-Methoxycarbonylamino-6-methylbenzyloxy)-2,3-dimethylimidazo[1,2-a]pyridine A solution of 9.5 g of 2-methoxycarbonylamino-6-methylbenzyl chloride in 150 ml of dry acetonitrile is added dropwise at RT to a suspension of 7.2 g of 8-hydroxy-2,3-dimethylimidazo[1,2-a]pyridine in 130 ml of dry acetonitrile, to which 8 g of commercial potassium fluoride (50% by weight) in kieselguhr (for example Celite®) has been added. The mixture is heated at 70° C. for 9 h. After cooling to RT, the mixture is poured into 1 l of ice-water and extracted three times with ethyl acetate. The collected organic phases are washed with distilled water and dried over sodium sulfate. After stripping off the organic solvent in vacuo, the precipitating residue is filtered off, washed with a little ethyl acetate and ether and dried. After recrystallization from isopropanol, 2.2 g of the title compound of m.p. 176°–177° C. are obtained.

7. 8-(6-Methyl-2-nitrobenzylamino)-2,3-dimethylimidazo[1,2-a]pyridine

Sodium iodide (15.0 g) and sodium carbonate (31.0 g) are added to a solution of 8-amino-2,3-dimethylimidazo[1,2-a]pyridine (14.7 g) and 6-methyl-2-nitrobenzylchloride (18.6 g) in acetone (100 ml) at RT and are heated to reflux for 6 h. After cooling to RT and evaporation of the solvent, the residue is dissolved in a mixture of ethyl acetate (200 ml) and water (200 ml), and the organic phase is separated off. After three further extractions with ethyl acetate (100 ml) the combined organic layers are dried over magnesium sulfate and concentrated to a volume of 80 ml. 12.1 g of the title compound crystallize as a faintly yellow solid. The mother liquor is evaporated and the residue is purified by chromatography on silica gel (toluene/dioxane=6:1 as eluent) to yield additional 14 g of crystalline material. After recrystallization of both fractions from ethyl acetate, 21.5 g (76%) of the title compound of m.p. 160°–162° C. are isolated.

8. 8-(2-tert-Butoxycarbonylamino-6-methylbenzylamino)-2,3-dimethylimidazo[1,2-a]pyridine The title compound is prepared according to the procedure described for example 1 starting from 8-amino-2,3-dimethylimidazo[1,2-a]pyridine (4.8 g), 2-tert-butoxycarbonylamino-6-methylbenzylchloride (9.2 g), sodium iodide (5.5 g) and sodium carbonate (8.0 g) in acetone (250 ml). Purification by chromatography on silica gel (toluene/dioxane 20:1 as eluent) and crystallization from diisopropyl ether yield 7.1 g (62%) of m.p. 149°–152° C.

9. 8-(2-tert-Butoxycarbonylamino-6-methylbenzylamino)-2,3-dimethylimidazo[1,2-a]pyridine The title compound is prepared according to the procedure described for example 7 starting from 2,3-dimethyl-8-hydroxy-imidazo[1,2-a]pyridine (1.6 g), 2-tert-butoxycarbonylamino-6-methylbenzylchloride (3.1 g), sodium iodide (1.8 g) and sodium carbonate (2.7 g) in acetone (350 ml). Purification by chromatography on silica gel (toluene/dioxane 5:1 as eluent) and crystallization from cyclohexane yield 3.0 g (78%) of m.p. 128°–131° C.

10. 8-(2-tert-Butoxycarbonylamino-6-methylbenzylamino)-3-formyl-2-methylimidazo[1,2-a]pyridine The title compound is prepared according to the procedure described for example 7 starting from 8-amino-3-formyl-2-methylimidazo[1,2-a]pyridine (4.0 g), 2-tert-butoxycarbonylamino-6-methylbenzylchloride (7.0 g), sodium iodide (4.1 g) and sodium carbonate (6.1 g) in acetone (250 ml). Purification by chromatography on silica gel (toluene/dioxane 9:1 as eluent) and crystallization from diisopropyl ether yield 7.3 g (81%) of m.p. 210°–212° C.

11. 8-(2-tert-Butoxycarbonylamino-6-methylbenzylamino)-3-formyl-2-methylimidazo[1,2-a]pyridine a) 4.77 g of 8-benzyloxy-2-methylimidazo[1,2-a]pyridine are stirred in a Vilsmeier mixture of 20 ml of dimethylformamide and 2.3 ml of phosphoryl chloride for 2.5 h at 60° C., and are worked up mit ice/water and potassium hydrogen carbonate in a usual manner. 8-Benzyloxy-2-methylimidazo[1,2-a]pyridine-3-carboxaldehyde of m.p. 105°–106° C. (from diisopropylether) is obtained, which is debenzylated according to Kaminski et al., J. Med. Chem. 28, 876 (1985), method H, to yield 3-formyl-8-hydroxy-2-methylimidazo[1,2-a]pyridine of m.p. 251°–252° C.

b) The title compound is prepared according to the procedure described for example 7 starting from 3-formyl-8-hydroxy-2-methylimidazo[1,2-a]pyridine (2.4 g), 2-tert-butoxycarbonylamino-6-methylbenzylchloride (4.2 g), sodium iodide (2.5 g) and sodium carbonate (3.7 g) in acetone (400 ml). Purification by crystallization from diisopropyl ether/ethyl acetate yield 4.4 g (80%) of m.p. 189°–191° C.

12. 8-(2-Amino-6-methylbenzylamino)-2,3-dimethylimidazo[1,2-a]pyridine

Method A:

A solution of 8-(6-methyl-2-nitrobenzylamino)-2,3-dimethylimidazo[1,2-a]pyridine (61 g) in methanol (5.5 l) is treated with 15 g of palladium on charcoal (5%) catalyst and hydrogenated at atmospheric pressure for 1.5 h at RT. The catalyst is filtered off and the solvent is evaporated. The residue is dissolved in boiling ethyl acetate (2.7 l). After cooling to RT, 51 g (82%) of the title compound of m.p. 206°–208° C. are isolated.

Method B:

8-(2-tert-Butoxycarbonylamino-6-methylbenzylamino)-2,3-dimethylimidazo-[1,2-a]pyridine (6.7 g) is added portionwise to a mixture of trifluoroacetic acid (30 ml) and anisole (3 ml) at 25°–30° C. After stirring for 30 minutes at RT the solution is added to ice-water (100 ml) and then treated with 6N sodium hydroxide solution (75 ml). The precipitate is filtered and purified by chromatography on silica gel (toluene/dioxane=8:1 as eluent). After crystallization from ethyl acetate, 3.1 g (62%) of the title compound of m.p. 206°–208° C. are isolated.

13. 8-(2-Amino-6-methylbenzyloxy)-3-formyl-2-methylimidazo[1,2-a]pyridine

Starting from 8-(2-tert.-butoxy-carbonylamino-6-methylbenzyloxy)-3-formyl-2-methylimidazo[1,2-a]pyridine (5.0 g) and trifluoroacetic acid (40 ml) and by using the procedure described for example 12 (method B), 3.57 g (96%) of the title compound of m.p. 144°–150° C. (dec.) are obtained.

14. 8-(2-Ethoxycarbonylamino-6-methylbenzylamino)-2,3-dimethylimidazo[1,2-a]pyridine Ethyl chloroformiate (0.65 g) dissolved in dichloromethane (10 ml) is added dropwise to a solution of 8-(2-Amino-6-methylbenzylamino)-2,3-dimethylimidazo[1,2-a]pyridine (0.98 g) in dichloromethane (50 ml) and stirred for 18 h at RT. The solution is then extracted with saturated aqueous sodium bicarbonate solution (40 ml), washed with water (40 ml) and evaporated. The residue is recrystallized from ethyl acetate/diisopropyl ether. 0.32 g (26%) of the title compound of m.p. 208°–210° C. (dec.) are isolated.

15. 8-(2-Isobutoxycarbonylamino-6-methylbenzylamino)-2,3-dimethylimidazo[1,2-a]pyridine The title compound is prepared according to the procedure described for example 14 starting from isobutyl chloroformiate (0.3 g) and 8-(2-Amino-6-methylbenzylamino)-2,3-dimethylimidazo[1,2-a]pyridine (0.56 g) in dichloromethane (50 ml). 0.22 g (29%) of the title compound of m.p. 144°–146° C. are isolated.

16. 8-(2-Isobutoxycarbonylamino-6-methylbenzylamino)-2,3-dimethylimidazo[1,2-a]pyridine The title compound is prepared according to the procedure described for example 14 starting from isopropyl chloroformiate (1.5 g) and 8-(2-Amino-6-methylbenzylamino)-2,3-dimethylimidazo[1,2-a]pyridine (0.98 g) in dichloromethane (50 ml). 0.32 g (25%) of the title compound are isolated.

17. 8-(2-tert-Butoxycarbonylamino-6-methylbenzylamino)-3-hydroxymethyl-2-methylimidazo[1,2-a]pyridine The title compound is prepared according to the procedure described for example 2 starting from 8-(2-tert-Butoxycarbonylamino-6-methylbenzylamino)-3-formyl-2-methylimidazo[1,2-a]pyridine (0.15 g) and sodium borohydride (15 mg) in methanol. 0.12 g of the title compound of m.p. 102°–104° C. are isolated.

18. 8-(2-tert-Butoxycarbonylamino-6-methylbenzylamino)-3-hydroxymethyl-2-methylimidazo[1,2-a]pyridine The title compound is prepared according to the procedure described for example 2 starting from 8-(2-tert-Butoxycarbonylamino-6-methylbenzyloxy)-3-formyl-2-methylimidazo[1,2-a]pyridine (0.20 g) and sodium borohydride (19 mg) in methanol. 0.17 g of the title compound of m.p. 140°–142° C. are isolated.

Industrial applicability

The compounds of the formula I and their salts have valuable pharmacological properties which make them industrially utilizable. They exhibit, in particular, a pronounced inhibition of gastric acid secretion and an excellent protective action on the stomach and intestines of warm-blooded species. In this respect the compounds according to the invention are distinguished by a great selectivity of action, a comparatively long duration of action, a good enteral efficacy, the absence of significant side effects and a wide therapeutic range.

By "protection of the stomach and intestines" is meant in this connection the prevention and treatment of gastrointestinal disorders, especially gastrointestinal inflammatory disorders and lesions (such as, for example, gastric ulcer, duodenal ulcer, gastritis, functional gastropathy due to hyperacidity or drugs) which may be caused, for example, by microorganisms (for example *Helicobacter pylori*), bacterial toxins, drugs (for example certain antiinflammatory and antirheumatic agents), chemicals (for example ethanol), gastric acid or stress situations.

In their excellent properties, the compounds according to the invention surprisingly prove to be distinctly superior, in various models in which the antiulcerogenic and the antisecretory properties are determined, to the known compounds of the prior art. Because of these properties, the compounds of the formula I and their pharmacologically compatible salts are outstandingly suitable for use in human and veterinary medicine, where they are particularly used for the treatment and/or prophylaxis of diseases of the stomach and/or intestine.

The invention therefore further relates to the compounds according to the invention for use for the treatment and/or prophylaxis of the abovementioned disorders.

The invention likewise embraces the use of the compounds according to the invention for the production of pharmaceuticals which are employed for the treatment and/ or prophylaxis of the abovementioned disorders.

The invention furthermore embraces the use of the compounds according to the invention for the treatment and/or prophylaxis of the abovementioned disorders.

The invention further relates to the pharmaceuticals which contain one or more compounds of the formula I and/or their pharmacologically compatible salts.

The pharmaceuticals are produced by processed which are known per se and familiar to the skilled worker. As pharmaceuticals, the pharmacologically active compounds (=active substances) according to the invention are employed either as such or, preferably, in combination with suitable pharmaceutical ancillary substances or vehicles in the form of tablets, coated tablets, capsules, suppositories, plasters (for example as TTS), emulsions, suspensions or solutions, wherein the content of active substance is advantageously between 0.1 and 95%, and wherein by appropriate choice of the ancillary substances and vehicles a pharmaceutical formulation (e.g. a sustained release formulation or an enteric formulation) can be obtained which fits exactly to the active substance and/or to the desired onset of effects.

The skilled worker is aware because of his expert knowledge which ancillary substances and vehicles are suitable for the required pharmaceutical formulations. Besides solvents, gel formers, suppository bases, tablet ancillary substances and other active substance vehicles, it is possible to use, for example, antioxidants, dispersants, emulsifiers, antifoam agents, flavour correctives, preservatives, solubilizers, colorants or, in particular, permeation promoters and complexing agents (for example cyclodextrins).

The active substances can be administered orally, parenterally or percutaneously.

In general, it has proven advantageous in human medicine to administer the active substance or substances on oral administration in a daily dose of about 0.01 to about 20, preferably 0.05 to 5, in particular 0.1 to 1.5 mg/kg of body weight, where appropriate in the form of a plurality, preferably 1 to 4, individual administrations to achieve the required result. In the case of parenteral treatment it is possible to use similar or (especially for intravenous administration of the active substances) as a rule lower dosage. The skilled worker is easily able because of his expert knowledge to establish the optimal dosage and mode of administration of the active substances required in each case.

If the compounds and/or salts according to the invention are to be employed for the treatment of the abovementioned disorders, the pharmaceutical preparations can also contain one or more pharmacologically active constituents from other groups of pharmaceuticals, such as antacids, for example aluminium hydroxide, magnesium aluminate; tranquilizers such as benzodiazepines, for example diazepam; spasmolytics such as, for example, bietamiverine, camylofin; anticholinergics such as, for example, oxyphencyclimine, phencarbamide; local anesthetics such as, for example, tetracaine, procaine; where appropriate also enzymes, vitamins or amino acids.

Particularly noteworthy in this connection is the combination of the compounds according to the invention with drugs which inhibit acid secretion, such as, for example, $H_2$ blockers (for example cimetidine, ranitidine), $H^+/K^+$ATPase inhibitors (for example omeprazole, pantoprazole), or furthermore with so-called peripheral anticholinergics (for example pirenzepine, telenzepine) and with gastrin antagonists with the aim of enhancing the principal action in an additive or superadditive sense and/or eliminating or reducing the side effects, or furthermore the combination with substances with antibacterial activity (such as, for example, cephalosporins, tetracyclines, nalidixic acid, penicillins or else bismuth salts) to control Helicobacter pylori.

Pharmacology

The excellent protective action on the stomach and the action inhibiting gastric acid secretion by the compounds according to the invention can be demonstrated in investigations on animal experimental models. The compounds according to the invention investigated in the model detailed hereinafter have been provided with numbers which correspond to the numbers of these compounds in the examples.

Examination of the secretion-inhibiting action on the perfused rat stomach

The effect of the compounds according to the invention after intraduodenal administration on the acid secretion stimulated by pentagastrin in the perfused rat stomach in vivo is represented in the following Table 1.

TABLE 1

| No. | Dose (μmol/kg) i.d. | Inhibition of acid secretion (%) |
|---|---|---|
| 2 | 6 | 100 |
| 4 | 10 | 100 |
| 5 | 3 | 100 |
| 6 | 3 | 100 |

Method

Anesthetized rats (CD rat, female, 200–250 g; 1.5 g/kg i.m. urethane) underwent tracheotomy and then opening of the abdomen by a median epigastric incision, and fixation of a PVC catheter transorally in the esophagus and another via the pylorus in such a way that the ends of the tubes just projected into the lumen of the stomach. The catheter leading out of the pylorus led via a lateral opening in the right abdominal wall to the outside.

After thorough irrigation (about 50–100 ml) of the stomach, physiological NaCl solution at 37° C. was passed through continuously (0.5 ml/min, pH 6.8–6.9; Brun-Unita I). The effluate was collected (25 ml measuring cylinder) at intervals each of 15 min and underwent determination of the pH (pH meter 632, glass electrode EA 147; Diameter=5 mm, Metrohm) and, by titration against a freshly prepared 0.01N NaOH to pH 7 (Dosimat 655 Metrohm), of the secreted HCl.

Gastric secretion was stimulated by continuous infusion of 1 μg/kg (=1.65 ml/h) i.v. pentagastrin (left femoral vein) about 30 min after the end of the operation (that is to say after determination of 2 preliminary fractions). The substances to be tested were administered intraduodenally in a liquid volume of 1 ml/kg 60 min after the start of the continuous infusion of pentagastrin.

The body temperature of the animals was kept constant at 37.8°–38° C. by infrared irradiation and a heated cushion (automatic stepless control via rectal temperature sensor).

The dose which led to a maximum inhibition of acid secretion by 100% is indicated in the Table.

Sheet of formulae

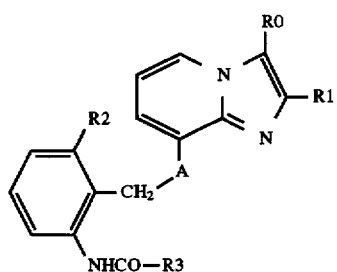

(I)

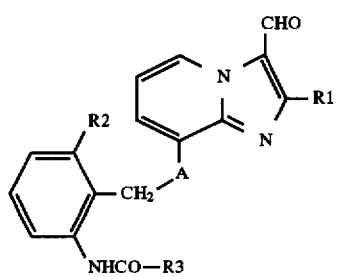

(II)

-continued
Sheet of formulae

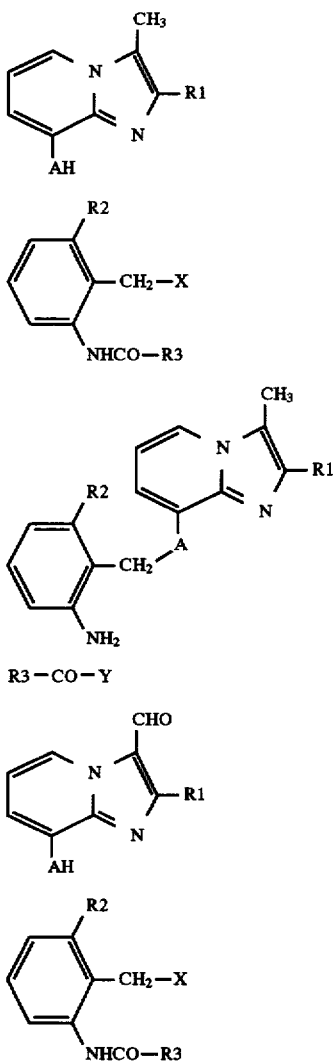

We claim:
1. A compound of formula I

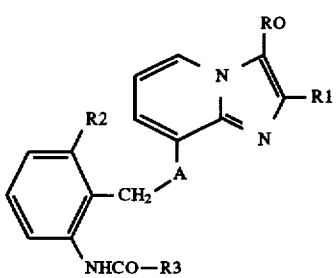

in which
R0 denotes methyl or hydroxymethyl,
R1 denotes 1–4C-alkyl,
R2 denotes 1–4C-alkyl,
R3 denotes 1–4C-alkoxy and
A denotes O (oxygen) or NH,
or a salt thereof.

2. A compound of formula I according to claim 1, wherein R0 denotes methyl.

3. A compound of formula I according to claim 1, wherein R0 denotes hydroxymethyl.

4. A compound according to claim 1 selected from the group consisting of

3-Hydroxymethyl-8-(2-methoxycarbonylamino-6-methylbenzylamino)-2-methyl-imidazo[1,2-a]pyridine,
3-Hydroxymethyl-8-(2-methoxycarbonylamino-6-methylbenzyloxy)-2-methyl-imidazo[1,2-a]pyridine,
8-(2-Methoxycarbonylamino-6-methylbenzyloxy)-2,3-dimethylimidazo[1,2-a]pyridine,
8-(2-tert-Butoxycarbonylamino-6-methylbenzylamino)-2,3-dimethylimidazo[1,2-a]pyridine,
8-(2-tert-Butoxycarbonylamino-6-methylbenzyloxy)-2,3-dimethylimidazo[1,2-a]pyridine,
8-(2-Ethoxycarbonylamino-6-methylbenzylamino)-2,3-dimethylimidazo[1,2-a]pyridine,
8-(2-Isobutoxycarbonylamino-6-methylbenzylamino)-2,3-dimethylimidazo[1,2-a]pyridine,
8-(2-Isopropoxycarbonylamino-6-methylbenzylamino)-2,3-dimethylimidazo[1,2-a]pyridine,
8-(2-tert-Butoxycarbonylamino-6-methylbenzylamino)-3-hydroxymethyl-2-methylimidazo[1,2-a]pyridine and
8-(2-tert-Butoxycarbonylamino-6-methylbenzyloxy)-3-hydroxymethyl-2-methylimidazo[1,2-a]pyridine or a salt thereof.

5. The compound of claim 1: 8-(2-Methoxycarbonylamino-6-methylbenzylamino)-2,3-dimethylimidazo[1,2-a]pyridine, or a salt thereof.

6. A process for the preparation of a compound of formula I as claimed in claim 1 and a salt thereof, which comprises a) for the preparation of a compound of formula I, in which R0 denotes hydroxymethyl, reducing compound of formula II

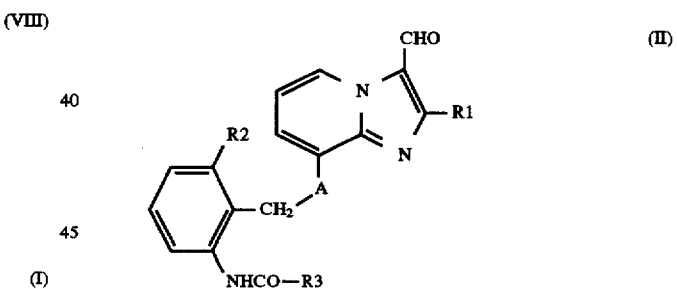

in which

R1, R2, R3 and A have the meanings given in claim 1, or comprises b) for the preparation of a compound of formula I, in which R0 denotes methyl, reacting a compound of formula III

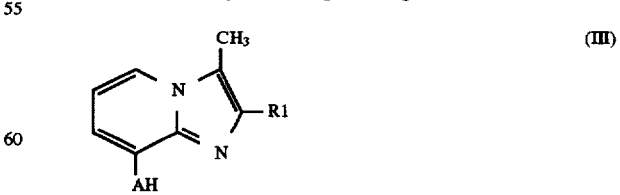

in which

R1 and A have the meanings given in claim 1, with a compound of formula IV

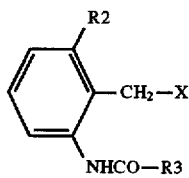

(IV)

in which

R2 and R3 have the meanings given in claim 1 and X denotes a suitable leaving group, or comprises c) for the preparation of a compound of formula I, in which R0 denotes methyl, reacting a compound of formula V

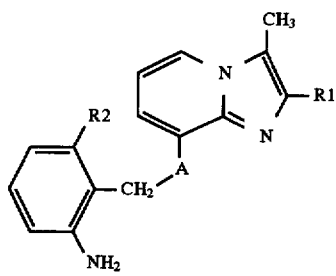

(V)

in which

R1, R2 and A have the meanings given in claim 1, with compound of formula VI $$R3—CO—Y \quad \text{(VI)}$$

wherein

R3 has the meaning given in claim 1 and Y denotes a suitable leaving group, and, if required, subsequently converting the resulting compound I into a salt thereof, or comprises, if required, subsequently liberating the compound I from a resulting salt of the compound I.

7. A pharmaceutical composition containing, in a suitable carrier, an effective amount of a compound as claimed in claim 1 and/or a pharmacologically compatible salt thereof.

8. A method for preventing or treating a gastrointestinal disorder which comprises administering an effective amount of a compound of claim 1 or a pharmacologically compatible salt thereof to one subject to or afflicted with such disorder.

9. In the compounding of a pharmaceutical composition comprising a suitable carrier and an essential active component for preventing or treating a gastrointestinal disorder, the improvement wherein the active component is a compound of claim 1 or a pharmacologically compatible salt thereof.

* * * * *